United States Patent
Drew (10) Patent No.: US 8,795,260 B2
(45) Date of Patent: Aug. 5, 2014

(54) REFILL OF IMPLANTABLE FLUID DELIVERY DEVICES BASED ON THERAPEUTIC FLUID EXPIRATION

(75) Inventor: Touby A. Drew, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 755 days.

(21) Appl. No.: 12/641,372

(22) Filed: Dec. 18, 2009

(65) Prior Publication Data

US 2011/0152756 A1 Jun. 23, 2011

(51) Int. Cl.
*A61M 5/168* (2006.01)

(52) U.S. Cl.
USPC .......... 604/890.1; 604/891.1; 604/892.1; 604/67

(58) Field of Classification Search
USPC ......... 604/890.1, 891.1, 892.1, 65, 67, 93.01; 700/215, 225, 299–300
See application file for complete search history.

(56) References Cited

U.S. PATENT DOCUMENTS

| 5,681,285 | A | 10/1997 | Ford et al. |
| 6,269,340 | B1 | 7/2001 | Ford et al. |
| 7,471,994 | B2 * | 12/2008 | Ford et al. ............... 700/282 |
| 7,775,056 | B2 * | 8/2010 | Lowenstein ............. 62/127 |
| 2004/0128162 | A1 | 7/2004 | Schlotterbeck et al. |
| 2004/0225252 | A1 | 11/2004 | Gillespie, Jr. et al. |
| 2006/0100746 | A1 | 5/2006 | Leibner-Druska |
| 2006/0200369 | A1 | 9/2006 | Batch et al. |
| 2006/0229551 | A1 | 10/2006 | Martinez et al. |
| 2007/0213598 | A1 | 9/2007 | Howard et al. |
| 2007/0271007 | A9 * | 11/2007 | Ali et al. ................. 700/900 |
| 2008/0071209 | A1 | 3/2008 | Moubayed et al. |
| 2009/0043290 | A1 * | 2/2009 | Villegas et al. ......... 604/891.1 |

FOREIGN PATENT DOCUMENTS

WO WO 03/095024 A2 11/2003

* cited by examiner

*Primary Examiner* — Quynh-Nhu H Vu
(74) *Attorney, Agent, or Firm* — Shumaker & Sieffert, P.A.

(57) ABSTRACT

An expiration time of a therapeutic fluid delivered by an implantable fluid delivery device is employed to calculate a fill volume and determine a refill interval for the fluid. The expiration time of the therapeutic fluid may be based on or dictated by a stability time set by the manufacturer of the therapeutic fluid, a clinician treating a patient to whom the fluid is to be delivered, the manufacturer of the device delivering the fluid, or combinations thereof.

15 Claims, 5 Drawing Sheets

REFILL OF IMPLANTABLE FLUID DELIVERY DEVICES BASED ON THERAPEUTIC FLUID EXPIRATION

TECHNICAL FIELD

This disclosure relates generally to implantable medical devices and, more particularly, to implantable fluid delivery systems.

BACKGROUND

A variety of medical devices are used for chronic, i.e., long-term, delivery of fluid therapy to patients suffering from a variety of conditions, such as chronic pain, tremor, Parkinson's disease, epilepsy, urinary or fecal incontinence, sexual dysfunction, obesity, spasticity, or gastroparesis. For example, pumps or other fluid delivery devices can be used for chronic delivery of therapeutic agents, such as drugs, to patients. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device that can deliver a fluid medication to a patient at a selected site. A drug infusion device may be implanted at a location in the body of a patient and deliver a fluid medication through a catheter to a selected delivery site in the body. Drug infusion devices, such as implantable drug pumps, commonly include a reservoir for holding a supply of a therapeutic fluid, such as a drug, for delivery to a site in the patient. The fluid reservoir can be self-sealing and accessible through one or more ports. A pump is fluidly coupled to the reservoir for delivering the therapeutic substance to the patient. A catheter provides a pathway for delivering the therapeutic substance from the pump to the delivery site in the patient.

SUMMARY

In general, this disclosure describes techniques for employing an expiration time of a therapeutic fluid delivered by a fluid delivery device to calculate a fill volume and/or determine a refill interval for refilling the device with the therapeutic fluid. The expiration time of the therapeutic fluid may be based on or dictated by a stability time. The stability time may be set, for example, by the manufacturer of the therapeutic fluid, a clinician treating a patient to whom the fluid is to be delivered, the manufacturer of the device delivering the fluid, or combinations thereof.

In one example, a fluid delivery system includes a fluid delivery device, a memory, and a processor. The fluid delivery device is at least partially implantable. The memory stores data including an expiration time for a therapeutic fluid configured to be stored in the fluid delivery device. The processor is configured to determine a refill interval for refilling the fluid delivery device with the therapeutic fluid based on the expiration time.

In another example, a method includes determining a refill interval for a therapeutic fluid delivered by a fluid delivery device based on an expiration time for the therapeutic fluid, and generating a refill indication based on the refill interval. In some examples, the refill indication may be a refill alarm that is generated, for example, in advance of expiration of the refill interval or upon expiration of the refill interval.

In one example, a programmer for an implantable fluid delivery device includes a memory and a processor. The memory stores data including an expiration time for a therapeutic fluid configured to be stored in the fluid delivery device. The processor is configured to calculate an amount of the therapeutic fluid to store in the fluid delivery device based on the expiration time for the therapeutic fluid.

In one more example, a method includes identifying a therapeutic fluid configured to be delivered by an implantable fluid delivery device, determining an expiration time for the therapeutic fluid, and calculating an amount of the therapeutic fluid to store in the fluid delivery device based on the expiration time.

The details of one or more examples disclosed herein are set forth in the accompanying drawings and the description below. Other features, objects, and advantages will be apparent from the description and drawings, and from the claims.

DETAILED DESCRIPTION

Medical devices are useful for treating, managing or otherwise controlling various patient conditions or disorders including, e.g., pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices, referred to herein generally as fluid delivery devices may be configured to deliver one or more fluid therapeutic agents, i.e., therapeutic fluids, alone or in combination with other therapies, such as electrical stimulation, to one or more target sites within a patient. For example, in some cases, a fluid delivery device may deliver pain-relieving drug(s) to patients with chronic pain, insulin to a patient with diabetes, or other fluids to patients with different disorders. The device may be implanted in the patient for chronic therapy delivery (i.e., longer than a temporary, trial basis) or temporary delivery.

Dosing program and therapy program generally refer to a program sent to an implantable fluid delivery device by a programming device to cause the fluid delivery device to deliver fluid at a certain rates and at a certain times. The dosing program may include, for example, definitions of a priming bolus, a supplemental bolus, and a therapy schedule. A dosing program may include additional information, such as patient information, permissions for a user to add a supplemental bolus, as well as limits on the frequency or number of such boluses, historical therapy schedules, fluid or drug information, or other information.

Therapy schedule generally refers to a rate (which may be zero) at which to administer a fluid, or a drug or drug combination within the fluid, at specific times to a patient. In particular, the therapy schedule may define one or more programmed doses, which may be periodic or aperiodic, each dose including, e.g., a rate of fluid delivery and a time duration for which to deliver the dose. Dose generally refers to the amount of drug or other therapeutic fluid delivered over a period of time, and may change over the course of a therapy schedule such that a drug or other therapeutic fluid may be delivered at different rates at different times. Although delivery of drugs may be described for purposes of illustration, the techniques described in this disclosure may be useful in delivery of various therapeutic fluids. Accordingly, description of the delivery of drugs should not be considered limiting with respect the techniques broadly described in this disclosure.

A priming bolus is a fluid pulse delivered by the implantable fluid delivery device to move the fluid non-therapeutically, commonly to the distal tip of the catheter, e.g., the tip of the catheter that is remote from the reservoir and internal tubing. Once the fluid is primed to the distal tip of the catheter, the device is ready to deliver fluid to the patient from the distal tip, e.g., via one or more fluid outlets at or near the distal tip. The device delivers the priming bolus during a priming phase to prepare the device for delivery of the fluid to the patient.

A supplemental bolus is a bolus administered to the patient outside of the therapy schedule. The terms independent bolus, one-time bolus, and therapeutic bolus may also be used in this disclosure to refer to a supplemental bolus. In one example, the implantable fluid delivery device may administer a supplemental bolus before the implantable fluid delivery device begins administering doses of fluid according to the therapy schedule. In another example, the implantable fluid delivery device may administer a supplemental bolus during the therapy schedule, e.g., to override or supplement the therapy schedule in response to clinician instruction or patient request.

One task required with implantable infusion therapy systems is determining when to refill the implantable fluid delivery device with additional therapeutic fluid. Implantable fluid delivery devices are commonly refilled based on the time it takes to deplete the therapeutic fluid stored in the device. In particular, refill intervals for fluid delivery systems are commonly determined based on the volume of therapeutic fluid within the device and the rate of delivery of the fluid, e.g., as determined by a therapy schedule, as well as patient or physician commanded boluses. However, some therapeutic fluids are delivered according to therapy programs that prescribe low dosages and/or infrequent delivery, which results in relatively slow depletion of the fluid stored in the device. Setting the time between refills based on volume-depletion alone in such circumstances may fail to account for time-dependent parameters that affect the therapeutic efficacy of the fluid. For example, some therapeutic fluids are delivered to patients so slowly that the time it takes to deplete the volume of fluid to a refill level exceeds a time period within which continued use of the fluid to treat the patient may be recommended or appropriate.

Therapeutic fluids delivered by implantable fluid delivery devices may be characterized by an expiration time, which generally refers to a limit on the amount of time the active agents in the therapeutic fluid retain their efficacy for treating a patient's condition. The expiration time for therapeutic fluids may depend on the chemical composition of the fluid, clinical aspects of treatments administered by the fluid, and/or non-clinical characteristics related to a particular fluid and may be expressed as a time duration, a discrete time stamp, e.g. a time and a date, a start and end time, or any other representation of the limit on the amount of time the active agents in the fluid retain their efficacy.

Expiration times for therapeutic fluids that depend on the chemical composition of the fluid generally relate to the stability of the fluid over time. Hence, in some cases, the expiration time also may be referred to as a stability time. As with expiration time, stability time may be expressed as a time duration, a discrete time stamp, e.g. a time and a date, a start and end time, or any other representation of the limit on the amount of time the active agents in the fluid remain stable. Some therapeutic fluids employed to treat patient conditions comprise a combination of substances that are chemically stable for a finite period of time. Drug stability is of particular concern for fluids that are administered at relatively slow rates/frequency and/or at low dosages such that the depletion of fluid volume in the implanted device extends beyond the stability time limit for the fluid. One example of a slowly administered therapeutic fluid is baclofen. Baclofen is a muscle relaxer and an antispastic agent, which is used to treat muscle symptoms caused by multiple sclerosis or spinal cord injury or disease, including spasm, pain, and stiffness.

Aside from chemical composition, the time limit on the stability of a therapeutic fluid is affected by a number of factors, such as environmental conditions. For example, the temperature at which the fluid is stored and the amount of light or other radiation it is subjected to may affect the stability time of the fluid. Additionally, the amount of time the fluid is stable after being deposited within an implanted fluid delivery device depends on the amount of time the fluid has been stored prior to being used. As the foregoing example of baclofen exhibits, the stability time of a fluid may be based on empirical data or evidence. In other examples, however, stability time may be based on an analytical limit dictated by a particular fluid composition, beyond which one or more constituents of the fluid simply break down or become otherwise unstable.

In addition to the stability of a fluid chemical composition, the expiration time of a therapeutic fluid may be based on clinical and non-clinical factors. For example, a clinician may set an expiration time based on a maximum amount of time between patient visits. In one such example, a clinician treats a cancer patient with chemotherapeutics delivered by an implanted fluid delivery device. However, the volume depletion based refill interval dictated by the amount of fluid in the device and the therapy schedule extends beyond the time the clinician wishes to prescribe between patient visits. The clinician may wish to limit the time between visits to monitor the degree to which the patient becomes desensitized to the chemotherapeutic being administered.

An example non-clinical factor that may affect or dictate expiration time of a therapeutic fluid is the actual experience a manufacturer has with the fluid. For example, a device manufacturer may employ a particular fluid in their devices only over a particular period of time between refills, e.g., in the course of clinical studies and regulatory (e.g., U.S. Food and Drug Administration (FDA)) approval of a drug delivery device. The refill interval with which the manufacturer actually has experience may or may not relate to the actual stability of the fluid, empirical or analytical, or clinical limits placed on the interval during the manufacturer's studies. In some examples, regardless of a reported or understood longer refill interval for the fluid, the manufacturer may nevertheless limit the expiration time to be within time periods with which the manufacturer has direct experience administering the fluid.

In light of the foregoing issues related to refill intervals, this disclosure presents techniques that are directed to determining refill intervals for therapeutic fluids delivered by implantable fluid delivery devices based on an expiration time for the fluid and facilitating the administration of fluid refills within such intervals. Additionally, the following examples include techniques for calculating a refill volume for a therapeutic fluid that is to be administered by an implantable fluid delivery device based on the expiration time, e.g., such that the fluid may be depleted at or before the expiration time, necessitating refill.

Figure 1:
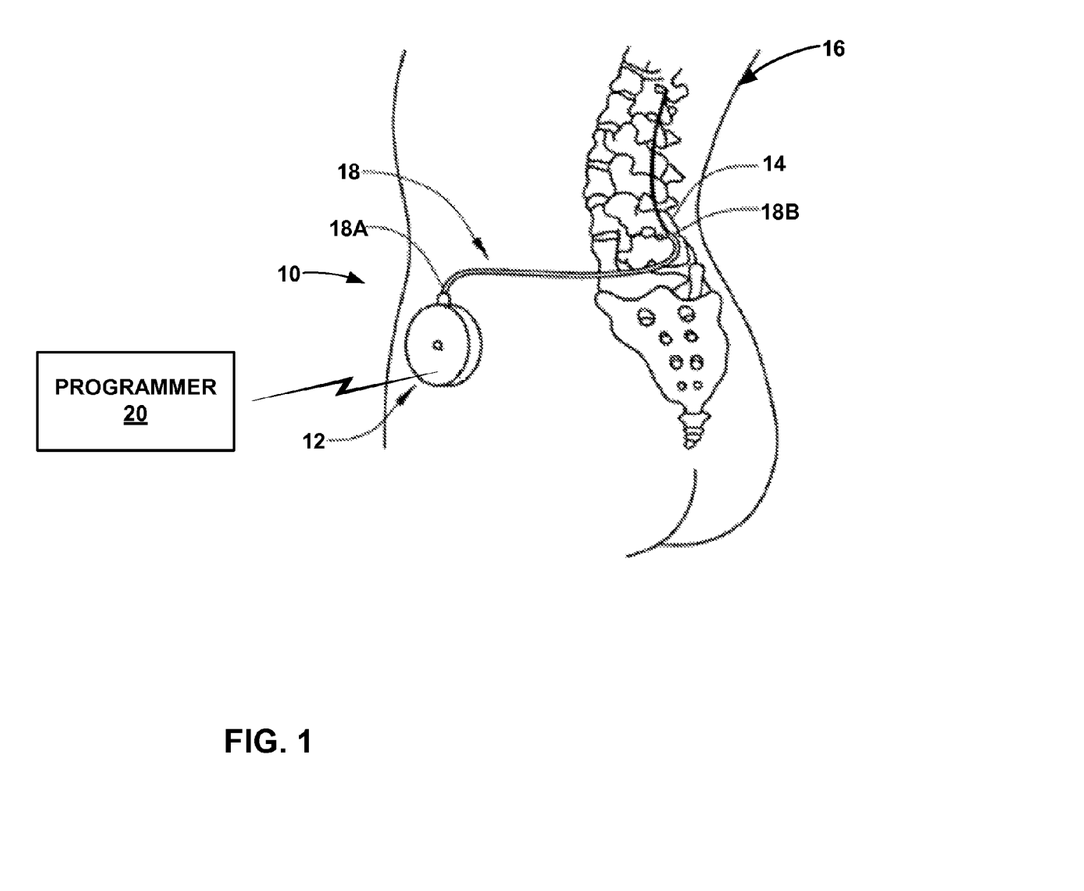
FIG. 1 is a conceptual diagram illustrating an example of a fluid delivery system including an implantable fluid delivery device configured to deliver a therapeutic fluid to a patient via a catheter.

FIG. 1 is a conceptual diagram illustrating an example of a therapy system 10, which includes implantable medical device (IMD) 12, catheter 18, and external programmer 20. Therapy system 10 may, in other examples, include additional components. For example, instead of being incorporated into IMD 12 as described below, therapy system may include an external or separately implanted telemetry module for communication between IMD 12 and programmer 20. In the example of FIG. 1, IMD 12 is connected to catheter 18 to deliver at least one therapeutic fluid agent, such as a pharmaceutical agent, pain relieving agent, anti-inflammatory agent, gene therapy agent, or the like, to a target site within patient 16. Example therapeutic agents that IMD 12 can be configured to deliver include, but are not limited to, insulin, morphine, hydromorphone, bupivacaine, clonidine, other analgesics, baclofen and other muscle relaxers and antispastic agents, genetic agents, antibiotics, nutritional fluids, hormones or hormonal drugs, gene therapy drugs, anticoagulants, cardiovascular medications or chemotherapeutics.

IMD 12 may include a reservoir, pump and controller for delivery of a therapeutic fluid via catheter 18. IMD 12 and catheter 18 together form an implantable fluid delivery device. In this case, the fluid delivery device is fully implantable within the patient, but may communicate with external devices such as programmer 20 via wireless telemetry, and receive refill of therapeutic fluid via percutaneous injection. In other examples, the fluid delivery device may be partially implantable. For example, the reservoir, pump and controller may be external to the patient, while catheter 18 may be implantable within the patient, and coupled to the external pump via a percutaneous port. Hence, the techniques described in this disclosure may be especially useful with fully implantable fluid delivery device including implantable reservoir, pump, controller and catheter, but also may be used with a partially implantable fluid delivery device.

In the example of FIG. 1, the therapeutic agent is a therapeutic fluid, which IMD 12 delivers to patient 16 through catheter 18 from proximal end 18A coupled to IMD 12 to distal end 18B located proximate to the target site. Catheter 18 can comprise a unitary catheter or a plurality of catheter segments connected together to form an overall catheter length. External programmer 20 is configured to wirelessly communicate with IMD 12 as needed, such as to provide or retrieve therapy information or control aspects of therapy delivery (e.g., modify the therapy parameters such as rate or timing of delivery, turn IMD 12 on or off, and so forth) from IMD 12 to patient 16.

IMD 12, in general, may have an outer housing that is constructed of a biocompatible material that resists corrosion and degradation from bodily fluids including, e.g., titanium or biologically inert polymers. IMD 12 may be implanted within a subcutaneous pocket relatively close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent. In still other examples, as discussed above, instead of providing fully implantable IMD 12, one or more components of IMD 12 may be external to patient 16 with a percutaneous catheter connected between such components and the target delivery site within patient 16, providing an at least partially implantable fluid delivery device. In general, however, fully implantable fluid delivery devices are described in this disclosure for purposes of illustration.

Catheter 18 may be coupled to IMD 12 either directly or with the aid of a catheter extension (not shown in FIG. 1). In the example shown in FIG. 1, catheter 18 traverses from the implant site of IMD 12 to one or more targets proximate to spine 14. Catheter 18 is positioned such that one or more fluid delivery outlets (not shown in FIG. 1) of catheter 18 are proximate to the targets within patient 16. In the example of FIG. 1, IMD 12 delivers a therapeutic agent through catheter 18 to targets proximate to spinal cord 14. IMD 12 can be configured for intrathecal drug delivery into the intrathecal space, as well as epidural delivery into the epidural space, both of which surround spinal cord 14. The epidural space (also known as "extradural space" or "peridural space") is the space within the spinal canal (formed by the surrounding vertebrae) lying outside the dura mater, which encloses the arachnoid mater, subarachnoid space, the cerebrospinal fluid, and spinal cord 14. The intrathecal space is within the subarachnoid space, which is further inward past the epidural space and dura mater and through the theca.

Although the target site shown in FIG. 1 is proximate to spinal cord 14 of patient 16, other applications of therapy system 10 include alternative target delivery sites. The target delivery site in other applications of therapy system 10 can be located within patient 16 proximate to, e.g., sacral nerves (e.g., the S2, S3, or S4 sacral nerves) or any other suitable nerve, organ, muscle or muscle group in patient 16, which may be selected based on, for example, a patient condition. In one such application, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve. Positioning catheter 18 to deliver a therapeutic fluid agent to various sites within patient 16 enables therapy system 10 to assist in managing, e.g., peripheral neuropathy or post-operative pain mitigation, ilioinguinal nerve therapy, intercostal nerve therapy, gastric drug induced stimulation for the treatment of gastric motility disorders and/or obesity, and muscle stimulation, or for mitigation of other peripheral and localized pain (e.g., leg pain or back pain). As another example delivery site, catheter 18 may be positioned to deliver a therapeutic agent to a deep brain site or within the heart (e.g., intraventricular delivery of the agent) or blood vessels. Delivery of a therapeutic agent within the brain may help manage any number of disorders or diseases including, e.g., chronic pain, diabetes, depression or other mood disorders, dementia, obsessive-compulsive disorder, migraines, obesity, and movement disorders, such as Parkinson's disease, spasticity, and epilepsy. Catheter 18 may also be positioned to deliver insulin to a patient with diabetes.

As already mentioned, in some applications, therapy system 10 can be used to reduce pain experienced by patient 16. In such an application, IMD 12 can deliver one or more therapeutic agents to patient 16 according to one or more dosing programs that set forth different therapy parameters, such as a therapy schedule specifying programmed doses, dose rates for the programmed doses, and specific times to deliver the programmed doses. The dosing programs may be a part of a program group for therapy, where the group includes a plurality of dosing programs and/or therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. Patient 16 or a clinician may select and/or generate additional dosing programs for use by IMD 12 via external programmer 20 at any time during therapy or as designated by the clinician.

In some examples, multiple catheters 18 may be coupled to IMD 12 to target the same or different tissue or nerve sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed in this disclosure with reference to the example of FIG. 1.

Programmer 20 is an external computing device that is configured to communicate with IMD 12 by wireless telemetry. For example, programmer 20 may be a clinician programmer that the clinician uses to communicate with IMD 12 and program therapy delivered by the IMD. Alternatively, programmer 20 may be a patient programmer that allows patient 16 to view and modify therapy parameters associated with therapy programs. The clinician programmer may include additional or alternative programming features than the patient programmer. For example, more complex or sensitive tasks may only be allowed by the clinician programmer to prevent patient 16 from making undesired or unsafe changes to the operation of IMD 12.

Programmer 20 may be a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone, personal computer, laptop, workstation computer, or personal digital assistant that can be configured with an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include hardware information for system 10 such as the type of catheter 18, the position of catheter 18 within patient 16, the type and amount, e.g., by volume of therapeutic agent(s) delivered by IMD 12, a refill interval for the therapeutic agent(s), a baseline orientation of at least a portion of IMD 12 relative to a reference point, therapy parameters of therapy programs stored within IMD 12 or within programmer 20, and any other information the clinician desires to program into IMD 12. In accordance with some examples of this disclosure, the refill interval may be based on an expiration time for the therapeutic agent(s).

The clinician uses programmer 20 to program IMD 12 with one or more therapy programs that define the therapy delivered by the IMD. During a programming session, the clinician may determine one or more dosing programs that may provide effective therapy to patient 16. Patient 16 may provide feedback to the clinician as to efficacy of a program being evaluated or desired modifications to the program. Once the clinician has identified one or more programs that may be beneficial to patient 16, the patient may continue the evaluation process and determine which dosing program or therapy schedule best alleviates the condition of the patient or otherwise provides efficacious therapy to the patient.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive supplemental boluses such as patient-initiated boluses (e.g., a lock-out interval), a maximum dose that may be delivered over a given time interval, and so forth. IMD 12 may include a feature that prevents dosing the therapeutic agent in a manner inconsistent with the dosing program. Programmer 20 may assist the clinician in the creation/identification of dosing programs by providing a methodical system of identifying potentially beneficial therapy parameters.

A dosage of a therapeutic agent, such as a drug, may be expressed as an amount of drug, e.g., measured in milligrams or other volumetric units, provided to patient 16 over a time interval, e.g., per day or twenty-four hour period. In this sense, the dosage may indicate a rate of delivery. This dosage amount may convey to the caregiver an indication of the probable efficacy of the drug and the possibility of side effects. In general, a sufficient amount of the drug should be administered in order to have a desired therapeutic effect, such as pain relief. However, the amount of the drug administered to the patient should be limited to a maximum amount, such as a maximum daily dose, in order to avoid potential side effects. Program information specified by a user via programmer 20 may be used to control dosage amount, dosage rate, dosage time, maximum dose for a given time interval (e.g., daily), or other parameters associated with delivery of a drug or other fluid by IMD 12. Dosage may also prescribe particular concentrations of active ingredients in the therapeutic agent delivered by IMD 12 to patient 16.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques. Programmer 20 may also communicate with another programmer or computing device via a wired or wireless connection using any of a variety of communication techniques including, e.g., RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks including, e.g., non-volatile memory. Further, programmer 20 may communicate with IMD 12 and another programmer via, e.g., a local area network (LAN), wide area network (WAN), public switched telephone network (PSTN), or cellular telephone network, or any other terrestrial or satellite network appropriate for use with programmer 20 and IMD 12.

In accordance with techniques described in this disclosure, therapy system 10 of FIG. 1 includes one or more processors configured to determine a refill interval for refilling IMD 12 with a therapeutic fluid based on an expiration time of the fluid. In some examples, IMD 12 may include multiple therapeutic fluids for individual or combined use to treat one or more conditions of patient 16, in which case such processor(s) may be configured to determine multiple refill intervals for the different fluids based on an expiration time for each fluid. Determination or prescription of expiration time and a refill interval based thereon may be implemented in IMD 12, programmer 20, or another electronic device including a processor and capable of communicating with IMD 12. In addition to determining a refill interval for the therapeutic fluid delivered by IMD 12, therapy system 10 may also facilitate refilling IMD 12 within the time interval by, e.g., generating a refill indication based on the refill interval. In some examples, the refill indication may be generated in advance of or upon expiration of the refill interval. For example, the refill indication may be generated at a predetermined period of time, e.g., several weeks, days, hours or minutes, prior to expiration of the refill interval, and/or at the time the refill interval expires. The refill indication may be an alarm or other notification or alert that is generated by IMD 12 and/or programmer 20 and communicated to patient 16 and/or a clinician in a variety of forms. For example, a refill alarm may include audible alerts issued by programmer 20 or another external device associated with therapy system 10. In another example, the refill alarm includes IMD 12 vibrating within the body of patient 16, thereby providing a tactile alert. In other examples, the refill alarm includes text or graphical messages delivered to patient 16 and/or a clinician via text message or e-mail from programmer 20 or another electronic device communicatively connected to IMD 12 and/or programmer 20, thereby providing a visual alert. In general, the refill interval may also be presented or referred to as low reservoir alarm threshold and the refill alarm may be presented or referred to as low reservoir alarm.

Although examples disclosed herein describe determining, and, in some instances, setting a refill interval for refilling an IMD with a therapeutic fluid based on an expiration time for the fluid, in some examples, a clinician may override any refill interval determined or set by the IMD or another device in communication with the IMD. For example, programmer 20 or IMD 12 may include one or more processors configured to determine a refill interval for refilling IMD 12 with a therapeutic fluid based on an expiration time of the fluid stored in a memory of and/or determined by the processor of the device. However, a clinician may nevertheless override the expiration time based refill interval determined by programmer 20 or IMD 12 by, e.g., inputting a refill interval into programmer 20, which the programmer may then communicate to IMD 12.

The expiration time(s) for the therapeutic fluid(s) delivered by IMD 12 may be based on or dictated by, e.g., a stability time set by the manufacturer of the therapeutic fluid, a clinician treating patient 16, the manufacturer of IMD 12, or combinations thereof. In some examples, expiration time for a therapeutic fluid depends on the stability of the chemical composition of the fluid over time, such as may be the case with, e.g., baclofen. In such examples, the expiration time of the fluid may be a set time period prescribed by the manufacturer of the fluid that is stored in a memory of IMD 12, programmer 20, and/or another device capable of communicating with IMD 12.

Parameters other than chemical composition that affect the stability of the therapeutic fluid with which IMD 12 is filled may also be programmed into IMD 12 and/or programmer 20 or otherwise incorporated into the expiration time for the fluid. For example, the environmental conditions, e.g. temperature or radiation exposure, under which the fluid is stored prior to use may be factored into the length of time the fluid will be stable after being loaded into IMD 12. Additionally, the stability based expiration time may account for the shelf-life of the therapeutic fluid. In some examples, a processor of IMD 12 may determine expiration time from the time the therapeutic fluid is loaded into IMD 12 based on a worst-case shelf-life assumption. The processor of IMD 12 (programmer 20 or another electronic device) assumes that the fluid has been on the shelf for the maximum period time allowed by the manufacturer before the fluid is to be used or discarded. IMD 12 then calculates the remaining time the therapeutic fluid will be stable by subtracting the shelf-life from the total prescribed stability time stored in a memory of IMD 12, programmer 20, and/or another device capable of communicating with IMD 12. In another example, a user, e.g. a clinician may employ programmer 20 or another device to input the actual time a therapeutic fluid has been on the shelf prior to being loaded into IMD 12.

In addition to or in lieu of stability based expiration time, expiration time may be set by a clinician treating patient 16. For example, a clinician may employ programmer 20 to set and communicate an expiration time to IMD 12 that does not necessarily relate to the stability of the therapeutic fluid. In some examples, the clinician sets the expiration time by programming the time into IMD 12 via programmer 20 or other remote electronic device communicatively connected to IMD 12 based on a maximum amount of time between clinic visits for patient 16. In one such example, patient 16 is treated by a clinician for cancer with chemotherapeutics delivered by an implanted fluid delivery device. However, the volume depletion-based refill interval dictated by the amount of fluid in the device and the therapy schedule by which the fluid is delivered to patient 16 extends beyond the time the clinician wishes to prescribe between patient visits. The clinician therefore limits the expiration time for the chemotherapeutic beyond the volume based refill interval. In this example, the clinician may limit the time between visits with patient 16, e.g., to monitor the degree to which the patient becomes desensitized to the chemotherapeutic being administered.

An example non-clinical factor that may affect or dictate expiration time of a therapeutic fluid is the actual experience a manufacturer has with the fluid. For example, the manufacturer of IMD 12 may employ only a limited number of therapeutic fluids over a particular period of time between refills in the course of clinical studies and FDA approval of IMD 12. The refill interval experienced by the manufacturer may or may not relate to the actual stability of the fluid, empirical or analytical, or clinical limits placed on the interval during the manufacturer's studies. In some such examples, therefore, regardless of a reported or understood longer refill interval for the fluid, the manufacturer of IMD 12 may nevertheless limit the expiration time tested therapeutic fluids to within time periods with which the manufacturer has direct experience administering the fluids. Such non-clinical expiration times may be set time periods prescribed by the device manufacturer and stored in a memory of IMD 12, programmer 20, and/or another device capable of communicating with IMD 12.

As described in the above examples, therapeutic fluid expiration time may be embodied as digital data stored in a memory of IMD 12, programmer 20, or another electronic device. The expiration time parameter may be associated with other parameters stored by IMD 12 and/or programmer 20 for a therapeutic fluid including, e.g., a name or other unique identifier of the fluid, manufacturer, active ingredients, concentration values and units, therapeutic effects, interactions with other substances, recommended dosage, daily low and/or high dosage limits, shelf-life, environmental storage criteria, side effects, on label and/or off label uses, the frequency of the use of the fluid by patient 16, and other parameters related to the character and use of the fluid. For example, one or both of IMD 12 and programmer 20 may include memory storing a digital drug library for a variety of therapeutic fluids that are, have been, or may be administered by IMD 12 and including a number of parameters, e.g. expiration time, for each of the fluids. Such drug libraries may be stored by IMD 12 and/or programmer 20 as a database, list, table, or other organized aggregation of digital data.

In some examples, IMD 12 and/or programmer 20 determine a refill interval for a therapeutic fluid delivered by IMD 12 based on both the fluid volume within IMD 12 and the expiration time of the fluid. In one such example, at some point in time including, e.g., prior to or during implantation within patient 16 or before or after a trial/programming period, IMD 12 is filled with a volume of therapeutic fluid the value of which is stored in a memory included in IMD 12. Also stored by IMD 12 is an expiration time for the fluid, which may be based on or dictated by, a stability time set by the manufacturer of the therapeutic fluid, a clinician treating patient 16, or the manufacturer of IMD 12.

IMD 12 determines a volume based refill interval for the fluid based on the amount of time it will take to deplete the fluid reservoir in IMD 12 to a set volume. The time to deplete the fluid volume will depend on the therapy schedule according to which IMD 12 is programmed to administer the fluid to patient 16, as well as rules related to supplemental boluses that may be administered by the patient. In one example, IMD 12 determines a fluid volume refill interval by using the maximum dosage that may be delivered by IMD 12 over time based on the programmed therapy schedule and the maximum number and amount of supplemental boluses allowed by the device. In other examples, instead of projecting future fluid depletion, IMD 12 may monitor a therapeutic fluid within a reservoir of the device over time by employing a sensor configured to measure the volume of the fluid in the reservoir.

In addition to a fluid volume refill interval, IMD 12 determines a refill interval for the therapeutic fluid based on an expiration time for the fluid. The expiration time may be stored in a memory of IMD 12 and/or programmer 20 and may be based on or dictated by, a stability time set by the manufacturer of the therapeutic fluid, a clinician treating patient 16, or the manufacturer of IMD 12. Thereafter, IMD 12 compares the volume-based and expiration time-based refill intervals to one another and, in some examples, sets the refill interval for the therapeutic fluid to the shorter of the two.

In addition to determining a refill interval for the therapeutic fluid delivered by IMD 12 and facilitating refilling IMD 12 within the determined time interval by generating a refill alarm upon expiration of the refill interval, therapy system 10 may also be configured to fill IMD 12 with a volume of therapeutic fluid that is calculated based on the expiration time of the fluid. In such examples, instead of employing an expiration time after IMD 12 is filled with the therapeutic fluid to determine a refill interval, expiration time is employed to determine the amount of fluid volume to load into IMD 12 for a particular refill interval. In this manner, expiration time may be employed proactively to reduce the amount of therapeutic fluid that is left unused in IMD 12 and thereby wasted upon expiration of the refill interval.

In one example, a therapeutic fluid with which IMD 12 is to be filled is identified. For example, a clinician or other user may enter the name or some unique identifier of the fluid into programmer 20, from which the programmer may cross-reference a drug library stored in a memory thereon or in IMD 12 to identify the fluid. Alternatively, the therapeutic fluid may be automatically identified by programmer 20 by reading a bar code on a container holding the fluid or communicating with and RFID tag connected thereto. After identifying the therapeutic fluid, programmer 20 or IMD 12 may reference a stored set of parameters including the expiration time for the fluid, e.g. stored in a drug library on a memory of the programmer or the IMD.

IMD 12 calculates the proper fill volume for the identified therapeutic fluid based on the expiration time and the volume of the fluid reservoir into which the fluid is to be filled. For example, IMD 12 calculates the amount of fluid volume depleted over the course of the expiration time based on the therapy schedule according to which IMD 12 is programmed to administer the fluid to patient 16, as well as rules related to supplemental boluses that may be administered by the patient. In the event the fluid volume that will be depleted over the expiration time is less than the volume of the reservoir of IMD 12 in which the fluid is to be filled, IMD 12 may set the fill volume for the fluid based on the expiration time. In the event, however, the fluid volume depleted over the expiration time is more than the volume of the reservoir of IMD 12 in which the fluid is to be filled, IMD 12 may set the fill volume equal to or less than the reservoir volume.

Figure 2:
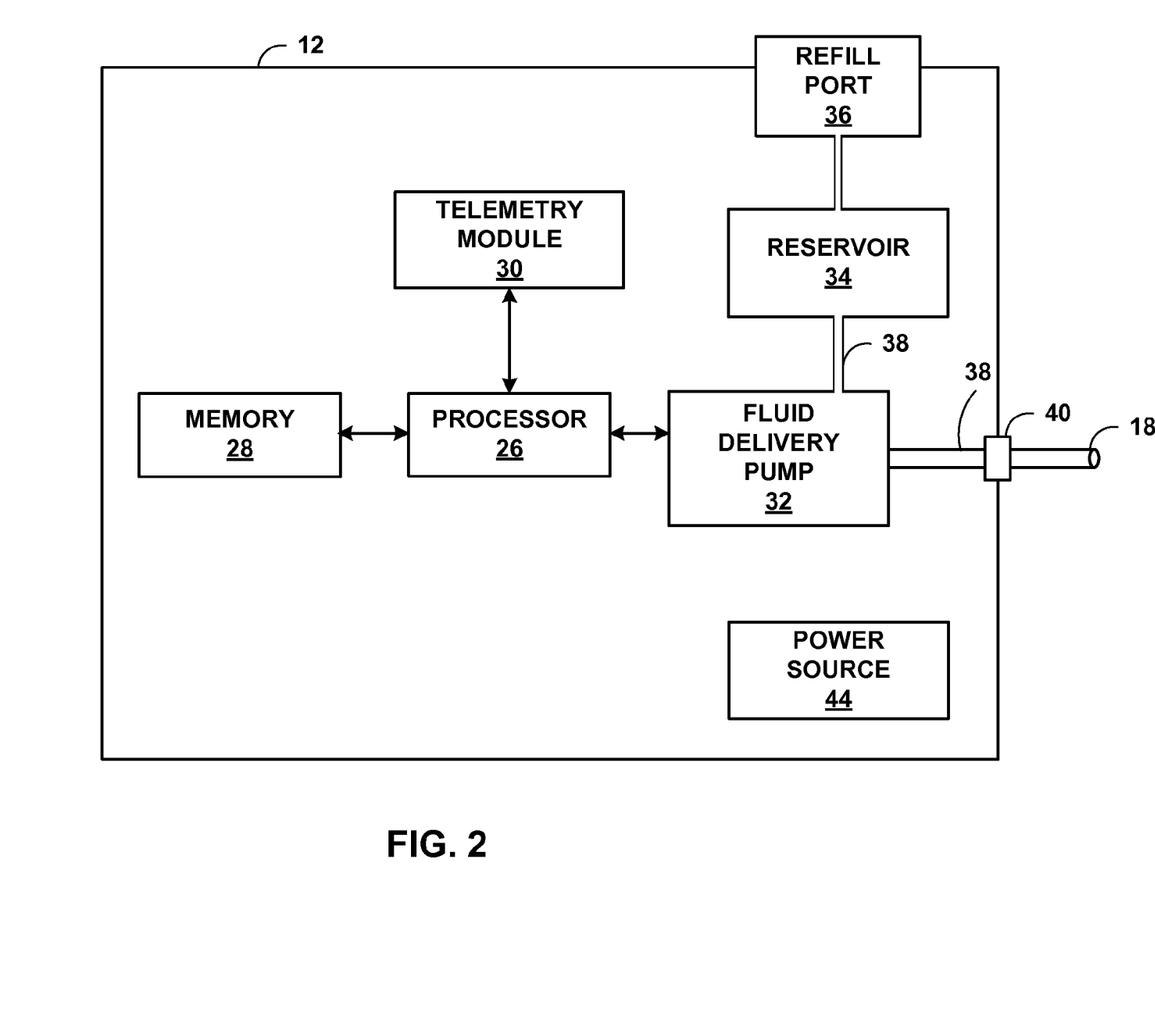
FIG. 2 is functional block diagram illustrating an example of the implantable fluid delivery device of FIG. 1.

FIG. 2 is a functional block diagram illustrating components of an example of IMD 12, which includes processor 26, memory 28, telemetry module 30, fluid delivery pump 32, reservoir 34, refill port 36, internal tubing 38, catheter access port 40, and power source 44. Processor 26 is communicatively connected to memory 28, telemetry module 30, and fluid delivery pump 32. Fluid delivery pump 32 is connected to reservoir 34 and internal tubing 38. Reservoir 34 is connected to refill port 36. Catheter access port 40 is connected to internal tubing 38 and catheter 18. IMD 12 also includes power source 44, which is configured to deliver operating power to various components of the IMD.

During operation of IMD 12, processor 26 operates as a controller that controls fluid delivery pump 32 with the aid of instructions associated with program information that is stored in memory 28 to deliver a therapeutic agent to patient 16 via catheter 18. Instructions executed by processor 26 may, for example, define dosing programs and/or therapy schedules that specify the amount of a therapeutic agent that is delivered to a target tissue site within patient 16 from reservoir 30 via catheter 18. The instructions may further specify the time at which the agent will be delivered and the time interval over which the agent will be delivered. The amount of the agent and the time over which the agent will be delivered are a function of, or alternatively determine, the dosage rate at which the fluid is delivered. The therapy programs may also include other therapy parameters, such as the frequency of bolus delivery, the type of therapeutic agent delivered if IMD 12 is configured to deliver more than one type of therapeutic agent, and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Upon instruction from processor 26, fluid delivery pump 32 draws fluid from reservoir 34 and pumps the fluid through internal tubing 38 to catheter 18 through which the fluid is delivered to patient 16 to effect one or more of the treatments described above. Internal tubing 38 is a segment of tubing or a series of cavities within IMD 12 that run from reservoir 34, around or through fluid delivery pump 32 to catheter access port 40. Fluid delivery pump 32 can be any mechanism that delivers a therapeutic agent in some metered or other desired flow dosage to the therapy site within patient 16 from reservoir 30 via implanted catheter 18.

In one example, fluid delivery pump 32 can be a squeeze pump that squeezes internal tubing 38 in a controlled manner, e.g., such as a peristaltic pump, to progressively move fluid from reservoir 34 to the distal end of catheter 18 and then into patient 16 according to parameters specified by a set of program information stored on memory 28 and executed by processor 26. Fluid delivery pump 32 can also be an axial pump, a centrifugal pump, a pusher plate, a piston-driven pump, or other means for moving fluid through internal tubing 38 and catheter 18. In one particular example, fluid delivery pump 32 can be an electromechanical pump that delivers fluid by the application of pressure generated by a piston that moves in the presence of a varying magnetic field and that is configured to draw fluid from reservoir 34 and pump the fluid through internal tubing 38 and catheter 18 to patient 16.

Periodically, fluid may need to be supplied percutaneously to reservoir 34 because all of a therapeutic agent has been or will be delivered to patient 16, or because a clinician wishes to replace an existing agent with a different agent or similar agent with different concentrations of therapeutic ingredients. Refill port 26 can therefore comprise a self-sealing membrane to prevent loss of therapeutic agent delivered to reservoir 30 via refill port 26. For example, after a percutaneous delivery system, e.g., a hypodermic needle, penetrates the membrane of refill port 26, the membrane may seal shut when the needle is removed from refill port 26. The time period between which a therapeutic fluid is refilled into reservoir 30 of IMD 12 via refill port 26, i.e. the refill interval for the fluid, may be based on one or both of the amount of fluid volume delivered to patient 16 by IMD 12 and the expiration time of the fluid.

In some examples, processor 26 of IMD 12 determines a refill interval for a therapeutic fluid delivered by IMD 12 based on both the fluid volume within reservoir 34 and the expiration time of the fluid. In one such example, at some point in time including, e.g., prior to or during implantation within patient 16 or before or after a trial/programming period, IMD 12 is filled with a volume of therapeutic fluid the value of which is stored in memory 28 of IMD 12. Also stored by IMD 12 is an expiration time for the fluid, which may be based on or dictated by, a stability time set by the manufacturer of the therapeutic fluid, a clinician treating patient 16, or the manufacturer of IMD 12. The expiration time parameter may be associated with other parameters for the therapeutic fluid stored in memory 28 as, e.g. a digital drug library that aggregates a number of parameters of a variety of therapeutic fluids that are, have been, or may be administered by IMD 12. Such drug libraries may be stored in memory 28 of IMD 12 as a database, list, table, or other organized aggregation of digital data.

Processor 26 of IMD 12 determines a volume based refill interval for a therapeutic fluid delivered by IMD 12 based on the amount of time it will take to deplete the fluid reservoir 34 to a set volume. The time to deplete the fluid volume will depend on the therapy schedule according to which IMD 12 is programmed to administer the fluid to patient 16, as well as rules related to supplemental boluses that may be administered by the patient, all of which may be stored in memory 28. In one example, processor 26 determines a fluid volume refill interval by using a maximum dosage that may be delivered by IMD 12 over time based on the programmed therapy schedule stored in memory 28 and the maximum number and amount of supplemental boluses allowed by the device according to patient bolus rules also stored in the memory of IMD 12. In other examples, instead of projecting future fluid depletion, processor 26 may be communicatively connected to a sensor configured to measure the volume of the fluid in reservoir 34. In such examples, processor 26 periodically polls the sensor for the volume of fluid remaining in reservoir 34.

In addition to a fluid volume refill interval, processor 26 of IMD 12 determines a refill interval for the therapeutic fluid based on an expiration time for the fluid. The expiration time may be stored in memory 28 and may be based on or dictated by, a stability time set by the manufacturer of the therapeutic fluid, a clinician treating patient 16, or the manufacturer of IMD 12. Thereafter, processor 26 may compare the volume-based and expiration time-based refill intervals stored in memory 28 and, in some examples, set the refill interval for the therapeutic fluid to the shorter of the two.

Although determining and setting a refill interval for a therapeutic fluid has been described as executed by IMD 12, and in particular, processor 26, in other examples one or more of these functions may be carried out by other devices including, e.g., external programmer 20. For example, one or both of the volume-based refill interval and expiration time-based refill interval may be determined by a processor of and stored on a memory of programmer 20. Additionally, the refill interval may be determined and/or set by programmer 20 based on a comparison of the volume and expiration time refill intervals to one another. In this example, programmer 20 then communicates the refill interval for the fluid to IMD 12 via telemetry module 30 and processor 26 stores the refill interval in memory 28.

In addition to storing therapeutic fluid expiration times and refill intervals based thereon, memory 28 of IMD 12 may store program information including instructions for execution by processor 26, such as, but not limited to, therapy programs, historical therapy programs, timing programs for delivery of fluid from reservoir 34 to catheter 18, and any other information regarding therapy of patient 16. A program may indicate the bolus size or flow rate of the drug, and processor 26 may accordingly deliver therapy. Memory 28 may include separate memories for storing instructions, patient information, therapy parameters (e.g., grouped into sets referred to as "dosing programs"), therapy adjustment information, program histories, and other categories of information such as any other data that may benefit from separate physical memory modules. Therapy adjustment information may include information relating to timing, frequency, rates and amounts of patient boluses or other permitted patient modifications to therapy. In some examples, memory 28 stores program instructions that, when executed by processor 26, cause IMD 12 and processor 26 to perform the functions attributed to them in this disclosure.

At various times during the operation of IMD 12 to treat patient 16, communication to and from IMD 12 may be necessary to, e.g., change therapy programs, adjust parameters within one or more programs, configure or adjust a particular bolus, or to otherwise download information to or from IMD 12. Processor 26 therefore controls telemetry module 30 to wirelessly communicate between IMD 12 and other devices including, e.g. programmer 20. Telemetry module 30 in IMD 12, as well as telemetry modules in other devices described in this disclosure, such as programmer 20, can be configured to use RF communication techniques to wirelessly send and receive information to and from other devices respectively. In addition, telemetry module 30 may communicate with programmer 20 via proximal inductive interaction between IMD 12 and the external programmer. Telemetry module 30 may send information to external programmer 20 on a continuous basis, at periodic intervals, or upon request from the programmer.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As another alternative, an external inductive power supply could transcutaneously power IMD 12 as needed or desired.

Figure 3:
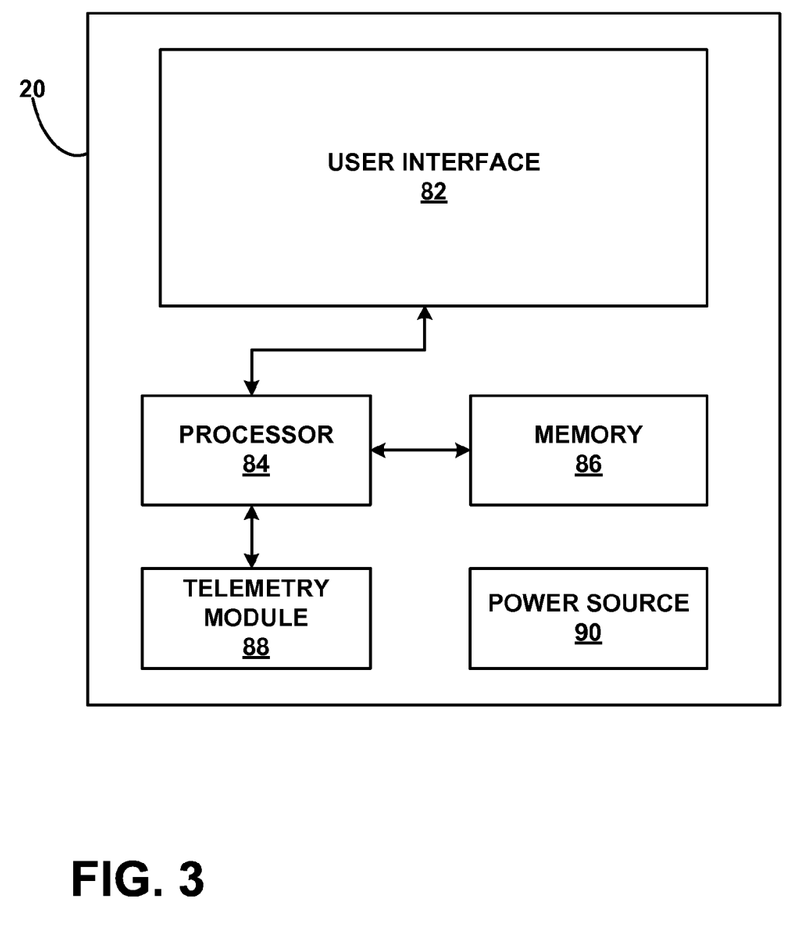
FIG. 3 is a functional block diagram illustrating an example of an external programmer as shown in FIG. 1.

FIG. 3 is a functional block diagram illustrating various components of external programmer 20 for IMD 12. As shown in FIG. 3, external programmer 20 includes user interface 82, processor 84, memory 86, telemetry module 88, and power source 90. A clinician or patient 16 interacts with user interface 82 in order to manually change the parameters of a dosing program, change dosing programs within a group of programs, view therapy information, view historical therapy regimens, establish new therapy regimens, or otherwise communicate with IMD 12 or view or edit programming information.

User interface 82 may include a screen and one or more input buttons, as discussed in greater detail below, that allow external programmer 20 to receive input from a user. Alternatively, user interface 82 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible indications of therapy program parameters or operational status, a display screen may suffice. For audible and/or tactile indications of therapy program parameters or operational status, programmer 20 may further include one or more audio speakers, voice synthesizer chips, piezoelectric buzzers, or the like.

Input buttons for user interface 82 may include a touch pad, increase and decrease buttons, emergency shut off button, and other buttons needed to control the therapy, as described above with regard to patient programmer 20. Processor 84 controls user interface 82, retrieves data from memory 86 and stores data within memory 86. Processor 84 also controls the transmission of data through telemetry module 88 to IMD 12. The transmitted data may include therapy program information specifying various drug delivery program parameters. Memory 86 may include operational instructions for processor 84 and data related to therapy for patient 16.

User interface 82 may be configured to present therapy program information to the user. User interface 82 enables a user to program IMD 12 in accordance with one or more dosing programs, therapy schedules, or the like. For example, a user such as a clinician, physician or other caregiver may input patient information, drug information including expiration time of the drug, therapy schedules, priming information, bridging information, drug/IMD implant location information, or other information to programmer 20 via user interface 82. In addition, user interface 82 may display therapy program information as graphical bar graphs or charts, numerical spread sheets, or in any other manner in which information may be displayed. Further, user interface 82 may present nominal or suggested therapy parameters that the user may accept via user interface 82.

Processor 84 of programmer 20 may be employed to determine and set a refill interval for a therapeutic fluid delivered by IMD 12. For example, one or both of a volume based refill interval and expiration time refill interval for a therapeutic fluid may be determined by processor 84 of programmer 20, alone or in conjunction with processor 26 of IMD 12. In one example, processor 84 stores the volume and expiration time based refill intervals in memory 86. Processor 84 may compare the volume-based time refill interval and the expiration time based refill interval stored in memory 86. In some examples, programmer 20 may set the refill interval for the therapeutic fluid to be delivered by IMD 12 to the shorter of the volume based time refill interval and the expiration time based refill interval based on the comparison performed by processor 84. Telemetry module 88 of programmer 20 then communicates the refill interval for the fluid to IMD 12 via telemetry module 30 and processor 26 stores the refill interval in memory 28.

In addition to employing programmer 20 to perform some or all of the functions associated with processor 26 of IMD 12 for determining expiration times and refill intervals based thereon, the programmer may also proactively calculate the appropriate fill volume of a therapeutic fluid to be delivered by the IMD 12 based on the expiration time of the fluid. In such examples, instead of employing an expiration time after IMD 12 is filled with the therapeutic fluid to determine a refill interval, expiration time is employed to determine the amount of fluid volume to load into IMD 12 for a particular refill interval. In this manner, expiration time may be employed proactively to reduce the amount of therapeutic fluid that is left unused in IMD 12 and thereby wasted upon expiration of the refill interval.

In one example, a therapeutic fluid with which IMD 12 is to be filled is identified using programmer 20. For example, a clinician or other user may enter the name or some unique identifier of the fluid into programmer 20, from which processor 84 may cross-reference a drug library stored in memory 86 or in memory 28 of IMD 12 to identify the fluid. Alternatively, the therapeutic fluid may be automatically identified by processor 84 after programmer 20 reads a bar code on a container holding the fluid or communicates with an RFID tag connected thereto. After identifying the therapeutic fluid, processor 84 references a stored set of parameters including the expiration time for the fluid, e.g. stored in a drug library on memory 86 of programmer 20 or memory 28 of IMD 12. In another example, the expiration time and other parameters associated with the therapeutic fluid are included in and thereby automatically determined by reading the bar code or communicating with the RFID tag on the fluid container.

Processor 84 of programmer 20, in this example, calculates the proper fill volume for the identified therapeutic fluid based on the expiration time and the volume of fluid reservoir 34 of IMD 12 into which the fluid is to be filled. For example, processor 84 calculates the amount of fluid volume depleted over the course of the expiration time based on a therapy schedule stored in memory 28 according to which IMD 12 is programmed to administer the fluid to patient 16, as well as rules also stored in memory 28 related to supplemental boluses that may be administered by the patient. Supplemental bolus rules stored in memory 28 of IMD 12 may be used by processor 84 by, e.g., assuming that patient 16 uses all of the boluses allowed by the device in a given period of time. Based on this worst-case assumption, processor 84 may determine the volume of fluid consumed by the supplemental boluses over a given period of time. In another example, processor 84 may use historical data stored in memory 28 (or memory 86 of programmer 20) to determine, e.g., an average number supplemental boluses used by patient 16 in a given period of time, e.g. in a day or a week. Processor 84 employs telemetry module 88 of programmer 20 to communicate with IMD 12 via telemetry module 30. In the event the fluid volume that will be depleted over the expiration time is less than the volume of reservoir 34, processor 84 may set the fill volume for the liquid based on the expiration time. In the event, however, the fluid volume depleted over the expiration time is more than the volume of reservoir 34, processor 84 may set the fill volume equal to or less than the reservoir volume. After the fill volume is calculated, processor 84 may store the parameter for the fluid in memory 86, as well as command telemetry module 88 to communicate with IMD 12 via telemetry module 30. Processor 84 may also control programmer 20 to display the fill volume to, e.g., a clinician who may then refer to the displayed value to properly fill IMD 12 with the therapeutic fluid.

Telemetry module 88 allows the transfer of data to and from IMD 12. Telemetry module 88 may communicate automatically with IMD 12 at a scheduled time or when the telemetry module detects the proximity of IMD 12. Alternatively, telemetry module 88 may communicate with IMD 12 when signaled by a user through user interface 82. To support RF communication, telemetry module 88 may include appropriate electronic components, such as amplifiers, filters, mixers, encoders, decoders, and the like. Power source 90 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12. Generally speaking, the techniques for determining and communicating refill intervals and fill volumes described in this disclosure may be communicated to and from IMD 12 via any type of external device capable of electronic communications therewith.

Figure 4:
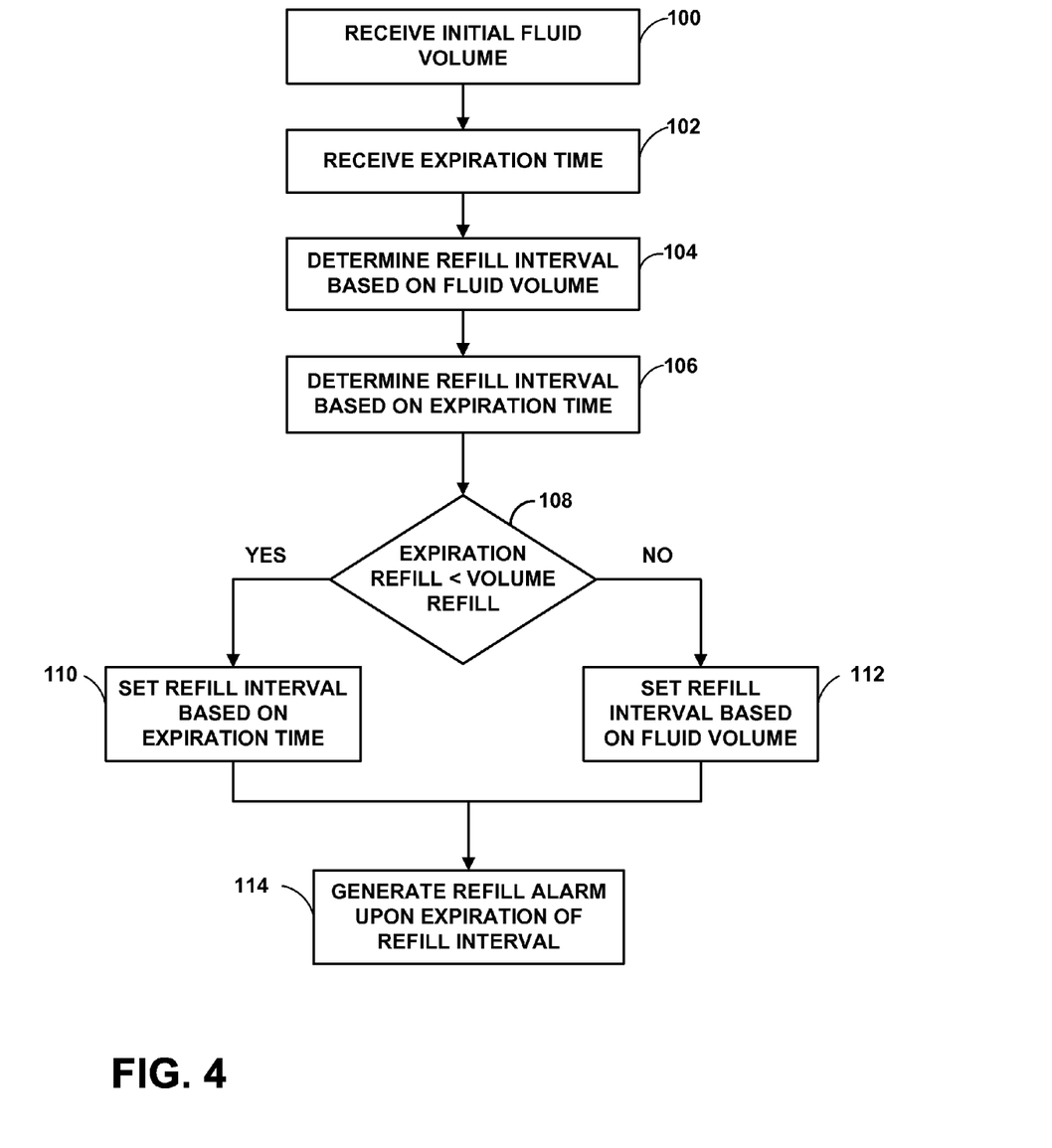
FIG. 4 is a flow chart illustrating an example method of refilling therapeutic fluids stored in a reservoir of a fluid delivery device.

FIG. 4 is a flow chart illustrating an example method of facilitating refills of therapeutic fluids stored in reservoirs of an implantable fluid delivery device, e.g. IMD 12. The method illustrated in FIG. 4 includes receiving an initial volume of a therapeutic fluid stored in a reservoir of an implantable fluid delivery device (100), receiving an expiration time for the therapeutic fluid (102), determining a refill interval based on the fluid volume (104), determining a refill interval based on the expiration time (106), comparing the fluid volume based refill interval to the expiration time-based refill interval to determine the lesser of the two intervals (108). If the expiration time-based refill interval is less than the fluid volume based refill interval, a refill interval for the therapeutic fluid may be set to the expiration time-based refill interval (110). If, however, the fluid volume based refill interval is less than the expiration time based refill interval, a refill interval for the therapeutic fluid may be set to the fluid volume based refill interval (112). Finally, a refill indication, such as an alarm, may be generated in advance of or, as indicated in the example of FIG. 4, upon expiration of the refill interval for the therapeutic fluid (114).

The method of FIG. 4 includes receiving an initial volume of a therapeutic fluid stored in a reservoir of an implantable fluid delivery device (100). For example, at some point in time including, e.g., prior to or during implantation of IMD 12 within patient 16 or before or after a trial/programming period, reservoir 34 of IMD 12 is filled with a volume of therapeutic fluid the value of which is stored in memory 28 of IMD 12. The fluid volume of the therapeutic fluid initially filled into reservoir 34 may be input by programmer 20, processor 84 of which may store the value in memory 86, as well as command telemetry module 88 to communicate the value to IMD 12 via telemetry module 30.

In addition to receiving an initial fluid volume (100), the method of FIG. 4 may include receiving an expiration time for the therapeutic fluid (102). The expiration time for the therapeutic fluid delivered by IMD 12 may be based on or dictated by, e.g., a stability time set by the manufacturer of the therapeutic fluid, a clinician treating patient 16, the manufacturer of IMD 12, or combinations thereof. In some examples, expiration time for a therapeutic fluid depends on the stability of the chemical composition of the fluid over time, such as may be the case with, e.g., baclofen. In such examples, the expiration time of the fluid may be a set time period prescribed by the manufacturer of the fluid that is stored in memory 28 of IMD 12, memory 86 of programmer 20, and/or in another electronic device capable of communicating with IMD 12. The expiration time of the therapeutic fluid may be associated in memory 28 and/or memory 86 with other parameters for the fluid including, e.g. a number of parameters for the fluid that are stored in a digital drug library for a variety of therapeutic fluids that are, have been, or may be administered by IMD 12. Such drug libraries may be stored by memory 28 of IMD 12 and/or memory 86 of programmer 20 as a database, list, table, or other organized aggregation of digital data.

Parameters other than chemical composition that affect the stability of the therapeutic fluid with which IMD 12 is filled may also be programmed into IMD 12 and/or programmer 20 or otherwise incorporated into a determination of the expiration time for the fluid. For example, the environmental conditions, e.g., temperature or radiation exposure, under which the fluid is stored prior to use may be factored into the length of time the fluid will be stable after being loaded into IMD 12. Additionally, the stability-based expiration time may account for the shelf-life of the therapeutic fluid. In some examples, processor 26 of IMD 12 or processor 84 of programmer 20 determines an expiration time from the time the therapeutic fluid is loaded into IMD 12 based on a worst-case shelf-life assumption. In some such examples, processor 26 assumes that the fluid has been on the shelf for the maximum period time allowed by the manufacturer before the fluid is to be used or discarded. Processor 26 then calculates the remaining time that the therapeutic fluid will be stable by subtracting the shelf-life from the total prescribed stability time stored in memory 28 of IMD 12, memory 86 of programmer 20, and/or another device capable of communicating with IMD 12.

In addition to or in lieu of stability-based expiration time, expiration time may be set by a clinician treating patient 16. For example, a clinician may employ programmer 20 to set and communicate an expiration time to IMD 12 that does not necessarily relate to the stability of the therapeutic fluid. In some examples, the clinician sets the expiration time by programming the time into IMD 12 via programmer 20 or other remote electronic device communicatively connected to IMD 12 based on a maximum allowed time between clinic visits for patient 16. In one such example, patient 16 is treated by a clinician for cancer with chemotherapeutics delivered by IMD 12 and the clinician limits the time between visits with patient 16 to monitor the degree to which the patient becomes desensitized to the chemotherapeutic being administered.

An example non-clinical factor that may affect or dictate expiration time of a therapeutic fluid is the actual experience a manufacturer has with the fluid. For example, the manufacturer of IMD 12 may employ only a limited number of therapeutic fluids only over a particular period of time between refills in the course of clinical studies and FDA approval of IMD 12. The refill interval experienced by the manufacturer may or may not relate to the actual stability of the fluid, empirical or analytical, or clinical limits placed on the interval during the manufacturer's studies. In some such examples, therefore, regardless of a reported or understood longer refill interval for the fluid, the manufacturer of IMD 12 may nevertheless limit the expiration time of tested therapeutic fluids to within time periods with which the manufacturer has direct experience administering the fluids. Such non-clinical expiration times may be set time periods prescribed by the device manufacturer and stored in memory 28 of IMD 12, memory 86 of programmer 20, and/or another device capable of communicating with IMD 12.

The method of FIG. 4 also includes determining a refill interval based on the fluid volume (104) and determining a refill interval based on the expiration time (106). In some examples, processor 26 of IMD 12 sets a refill interval for a therapeutic fluid delivered by IMD 12 based on both the fluid volume within reservoir 34 and the expiration time of the fluid. In one such example, at some point in time including, e.g., prior to or during implantation within patient 16 or before or after a trial/programming period, IMD 12 is filled with a volume of therapeutic fluid the value of which is stored in memory 28 of IMD 12. Also stored by IMD 12 in memory 28 is an expiration time for the fluid, which may be based on or dictated by, a stability time set by the manufacturer of the therapeutic fluid, a clinician treating patient 16, or the manufacturer of IMD 12. The expiration time parameter may be associated with other parameters for the therapeutic fluid stored in memory 28 as, e.g., a digital drug library that aggregates a number of parameters of a variety of therapeutic fluids that are, have been, or may be administered by IMD 12.

Processor 26 of IMD 12 determines a volume-based refill interval (104) for a therapeutic fluid delivered by IMD 12 based on the amount of time it will take to deplete the fluid reservoir 34 to a set volume, which may be a zero or non-zero volume. The time to deplete the fluid volume will depend on the therapy schedule selected to control IMD 12 to administer the fluid to patient 16. In some cases, the time to deplete the fluid volume also may depend on rules related to supplemental boluses that may be administered by the patient, all of which may be stored in memory 28. In one example, processor 26 determines a fluid volume refill interval by using a maximum dosage that may be delivered by IMD 12 over time based on the programmed therapy schedule stored in memory 28 and the maximum number and amount of supplemental boluses allowed by the device according to patient bolus rules also stored in the memory of IMD 12.

In addition to a fluid volume refill interval, processor 26 of IMD 12 determines a refill interval for the therapeutic fluid based on an expiration time for the fluid (106). As described above with reference to receiving an expiration time for the therapeutic fluid (102), the expiration time may be stored in memory 28 a stability time set by the manufacturer of the therapeutic fluid, a clinician treating patient 16, or the manufacturer of IMD 12. In some examples, therefore, processor 26 determines the expiration time (106) by retrieving a set time period stored in a memory 28 of IMD 12, memory 86 of programmer 20, and/or another device capable of communicating with IMD 12.

In other examples, further processing may be required to determine the expiration time (106). Processor 26 may, for example, account for parameters other than chemical composition that affect the stability of the therapeutic fluid with which IMD 12 is filled in the determination of an expiration time based refill interval (106). For example, the environmental conditions, e.g. temperature or radiation exposure, under which the fluid is stored prior to use may be factored into the length of time the fluid will be stable after being loaded into IMD 12. Additionally, a stability based expiration time may need to account for the shelf-life of the therapeutic fluid. In some examples, processor 26 determines expiration time from the time the therapeutic fluid is loaded into IMD 12 based on a worst-case shelf-life assumption or based on the actual time the fluid is on the shelf as input by, e.g., a clinician. Processor 26 assumes that the fluid has been on the shelf for the maximum period of time allowed by the manufacturer before the fluid is to be used or discarded. Processor 26 then calculates the remaining time the therapeutic fluid will be stable by subtracting the shelf-life from the total prescribed stability time stored in, e.g., memory 28.

In addition to determining volume based and expiration time based refill intervals, processor 26 of IMD 12 compares the two refill intervals, e.g., stored in memory 28 (108). For example, processor 26 may compare the fluid volume based refill interval to the expiration time based refill interval to determine the lesser of the two intervals. If the expiration time based refill interval is less than the fluid volume based refill interval, processor 26 sets the refill interval for the therapeutic fluid is set to the expiration time based refill interval (110). If, however, the fluid volume based refill interval is less than the expiration time based refill interval, processor 26 sets the refill interval for the therapeutic fluid to the fluid volume based refill interval (112).

In other embodiments, instead of setting the refill interval automatically, processor 26 may cause the volume based refill interval and the expiration time based refill interval to be displayed, e.g., on programmer 20 for review by a user, such as a clinician. Based on the two values, the clinician may then set the refill interval for the fluid.

Processor 26 of IMD 12 may cause a refill indication, such as an alarm, to be generated in advance, or upon expiration, of the refill interval for the therapeutic fluid. In the example of FIG. 4, a refill alarm is generated upon expiration of the refill interval (114). The alarm may be generated by processor 26 and/or processor 84 of programmer 20 and communicated to patient 16 and/or a clinician in a variety of forms. For example, the refill alarm may include audible alerts issued by programmer 20 or another external device associated with therapy system 10. In another example, the refill alarm includes IMD 12 vibrating within the body of patient 16. In other examples, the refill alarm includes text or graphical messages delivered to patient 16 and/or a clinician via, e.g., text message or e-mail.

Figure 5:
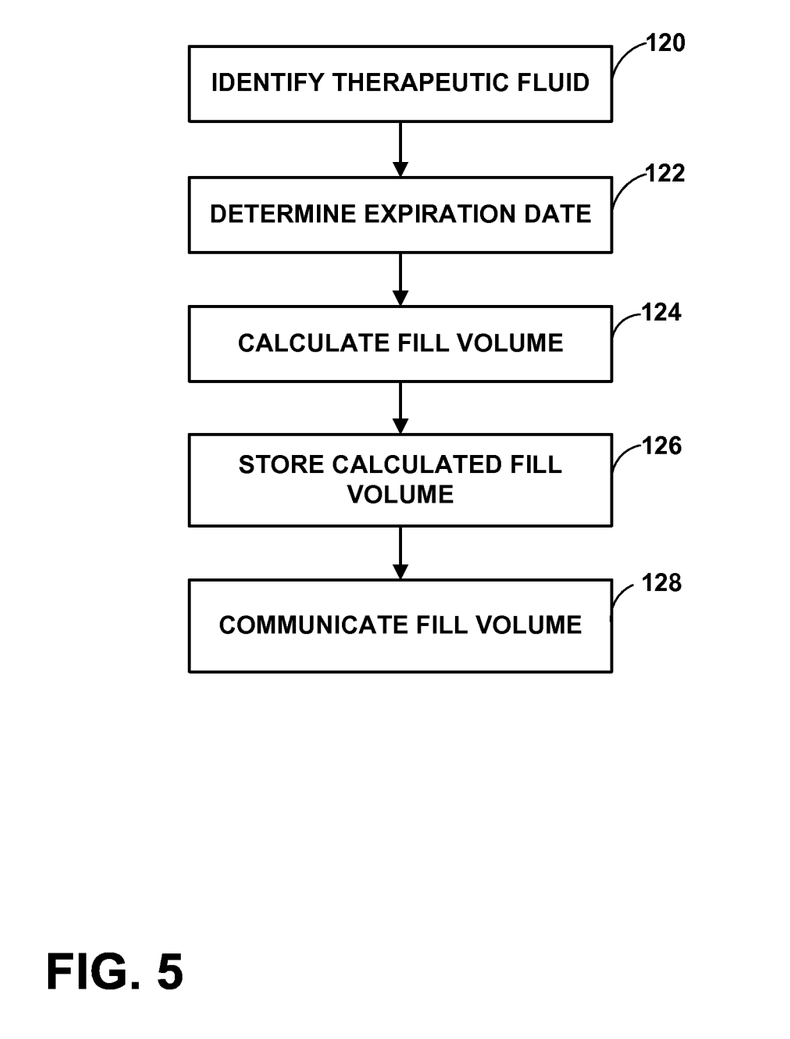
FIG. 5 is a flow chart illustrating an example method of filling a fluid delivery device with a therapeutic fluid.

FIG. 5 is a flow chart illustrating an example method of facilitating filling an implantable fluid delivery device, e.g. IMD 12 with a therapeutic fluid. The method illustrated in FIG. 5 includes identifying a therapeutic fluid configured to be delivered by an implantable fluid delivery device (120), determining an expiration time for the therapeutic fluid (122), calculating an amount of the therapeutic fluid to store in the fluid delivery device based on the expiration time (124), and storing and communicating the calculated refill volume (126, 128).

In some examples, programmer 20 may proactively calculate the appropriate fill volume of a therapeutic fluid to be delivered by IMD 12 based on the expiration time of the fluid. In such examples, instead of employing an expiration time after IMD 12 is filled with the therapeutic fluid to determine a refill interval, expiration time is employed to determine the amount of fluid volume to load into IMD 12 for a particular refill interval. In this manner, expiration time may be employed proactively to reduce the amount of therapeutic fluid that is left unused in IMD 12 and thereby wasted upon expiration of the refill interval.

In one example, a therapeutic fluid with which IMD 12 is to be filled is identified using programmer 20 (120). For example, a clinician or other user may enter the name or some unique identifier of the fluid into programmer 20, from which processor 84 may cross-reference a drug library stored in memory 86 or in memory 28 of IMD 12 to identify the fluid. In another example, the therapeutic fluid is automatically identified by processor 84 after programmer 20 reads a bar code on a container holding the fluid or communicates with an RFID tag connected thereto.

In addition to identifying the therapeutic fluid (120), processor 84 determines the expiration time for the fluid (122) by referencing a set of parameters stored in memory 86 or memory 28 of IMD 12, e.g. stored in a drug library. In another example, the expiration time and other parameters associated with the therapeutic fluid are included in and thereby automatically determined by reading the bar code or communicating with the RFID tag on the fluid container.

Processor 84 of programmer 20 calculates the proper fill volume for the identified therapeutic fluid (124) based on the expiration time and the volume of fluid reservoir 34 of IMD 12 into which the fluid is to be filled. For example, processor 84 calculates the amount of fluid volume depleted over the course of the expiration time based on a therapy schedule stored in memory 28 according to which IMD 12 is programmed to administer the fluid to patient 16, as well as rules also stored in memory 28 related to supplemental boluses that may be administered by the patient. Processor 84 employs telemetry module 88 of programmer 20 to communicate with IMD 12 via telemetry module 30. In the event the fluid volume that will be depleted over the expiration time is less than the volume of reservoir 34, processor 84 sets the fill volume for the liquid based on the expiration time. In the event, however, the fluid volume depleted over the expiration time is more than the volume of reservoir 34, processor 84 sets the fill volume equal to or less than the reservoir volume. After the fill volume is calculated, processor 84 may store the fill volume for the fluid in memory 86 (126), as well as control telemetry module 88 to communicate with IMD 12 via telemetry module 30 (128). In another example, processor 84 of programmer 20 may communicate the fill volume to IMD 12 and store the parameter on memory 28 in addition to or in lieu of storing the parameter on memory 86. In one more example, processor 84 may communicate the fill volume (128) by displaying the parameter on programmer 20 or otherwise communicating the fill volume to a user via an electronic device.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described herein. These and other examples are within the scope of the following claims.

The invention claimed is:

1. A method comprising:
   determining a refill interval for a therapeutic fluid delivered by a fluid delivery device based on an expiration time for the therapeutic fluid; wherein the expiration time comprises a period of time prescribed by a clinician; and generating a refill indication based on the refill interval.

2. The method of claim 1, wherein generating a refill indication comprises generating a refill alarm upon expiration of the refill interval.

3. The method of claim 1, wherein generating a refill indication comprises generating a refill alarm in advance of expiration of the refill interval.

4. The method of claim 1, wherein the expiration time comprises a stability time for the therapeutic fluid.

5. The method of claim 1, further comprising determining a modified expiration time based on one or more environmental conditions under which the therapeutic fluid is stored and determining the refill interval for the therapeutic fluid delivered by the fluid delivery device based on the modified expiration time for the therapeutic fluid.

6. The method of claim 1, further comprising determining a modified expiration time based on a shelf-life of the therapeutic fluid and determining the refill interval for the therapeutic fluid delivered by the fluid delivery device based on the modified expiration time for the therapeutic fluid.

7. The method of claim 1, wherein the expiration time comprises a period of time prescribed by a manufacturer of the fluid delivery device based on empirical data for the therapeutic fluid.

8. The method of claim 1, wherein generating the refill indication comprises generating an alarm comprising one of an audible, tactile, or visual alert.

9. The method of claim 1, wherein generating the refill indication comprises vibrating the fluid delivery device.

10. The method of claim 1, wherein determining a refill interval for a therapeutic fluid delivered by a fluid delivery device based on an expiration time for the therapeutic fluid comprises:
   determining a refill interval based on a volume of the therapeutic fluid to be stored in the fluid delivery device;
   comparing the fluid volume based refill interval to the expiration time;
   and at least one of setting the refill interval for the therapeutic fluid to the lesser of the fluid volume based refill interval and the expiration time or displaying the volume based refill interval and the expiration time.

11. The method of claim 1, wherein the fluid delivery device is at least partially implantable.

12. The method of claim 1, wherein the fluid delivery device comprises a fluid delivery pump and an implantable catheter connected to the fluid delivery pump and configured to deliver the therapeutic fluid to a patient.

13. The method of claim 12, wherein the fluid delivery pump comprises one of an external or implantable fluid delivery pump.

14. A method comprising:
   determining a refill interval for a therapeutic fluid delivered by a fluid delivery device based on an expiration time for the therapeutic fluid; and
   generating a refill indication based on the refill interval, wherein generating the refill indication comprises vibrating the fluid delivery device.

15. A method comprising:
   determining a refill interval for a therapeutic fluid delivered by a fluid delivery device based on an expiration time for the therapeutic fluid; wherein determining the refill interval comprises determining the refill interval based on a volume of the therapeutic fluid to be stored in the fluid delivery device; comparing the fluid volume based refill interval to the expiration time; and at least one of setting the refill interval for the therapeutic fluid to the lesser of the fluid volume based refill interval and the expiration time or displaying the volume based refill interval and the expiration time; and
   generating a refill indication based on the refill interval.

* * * * *